United States Patent [19]
Ito et al.

[11] Patent Number: 6,132,373
[45] Date of Patent: Oct. 17, 2000

[54] INTIMA-MEDIA THICKNESS MEASURING APPARATUS AND ARTERIAL SCLEROSIS DIAGNOSING SYSTEM

[76] Inventors: Masao Ito, Room 406, Yamasho Building, 56-4 Higashinakano 1-chome, Nakano-ku, Tokyo-to; Yoshimitsu Yamasaki, 27-15-103, Hinoike-cho, Nishinomiya-shi, Hyogo-ken, both of Japan

[21] Appl. No.: 09/311,734

[22] Filed: May 14, 1999

[30] Foreign Application Priority Data

May 18, 1998 [JP] Japan .................... 10-135287

[51] Int. Cl.[7] ........................................ A61B 8/00
[52] U.S. Cl. .......................................... 600/437; 600/450
[58] Field of Search .................... 600/437, 440, 600/441, 447, 449, 450, 455–456, 463, 466–467

[56] References Cited

U.S. PATENT DOCUMENTS

| | | | |
|---|---|---|---|
| 5,109,859 | 5/1992 | Jenkins ................... | 600/463 X |
| 5,109,861 | 5/1992 | Walinsky et al. .......... | 600/467 X |
| 5,115,814 | 5/1992 | Griffith et al. ........... | 600/439 X |
| 5,148,809 | 9/1992 | Biegelesen-Knight et al. | 600/443 |
| 5,197,019 | 3/1993 | Delon-Martin et al. ..... | 600/443 |
| 5,203,337 | 4/1993 | Feldman ................. | 600/407 X |
| 5,520,185 | 5/1996 | Soni et al. .............. | 600/444 |
| 5,800,356 | 9/1998 | Criton et al. ............ | 600/441 |
| 5,857,973 | 1/1999 | Ma et al. ................ | 600/441 |
| 5,929,990 | 7/1999 | Nachtony et al. ......... | 600/443 |

OTHER PUBLICATIONS

S. Kanters et al., "Reproducibility of In Vivo Carotid Intima–Media Thickness Measurements", *Stroke,* vol. 28, No. 3, 1997, pp. 665–671.

R. Kawamori et al., "Prevalence of Carotid Atherosclerosis in Diabetic Patients", *Diabetes Care,* vol. 15, No. 10, 1992, pp. 1290–1294.

I. Wendehag et al., "A New Automated Computerized Analyzing System Simplifies Readings and Reduces the Variability in Ultrasound Measurement of Intima–Media Thickness", *Stroke,* vol. 28, No. 11, 1997, pp. 2195–2200.

*Primary Examiner*—Francis J. Jaworski
*Attorney, Agent, or Firm*—Young & Thompson

[57] ABSTRACT

An apparatus for measuring an intima-media thickness of a blood vessel is disclosed. The apparatus includes: an ultrasound device for outputting digital image data representing an image of the blood vessel produced by scanning the blood vessel with an ultrasound; and a data analyzing device for receiving the output digital image data and calculating the intima-media thickness of the blood vessel according to the received digital image data. The digital image data includes a plurality of luminance values each corresponding to respective one of a plurality of pixels of the image. The data analyzing device includes: a setting device for setting a base position between a center of the blood vessel and a position in a vicinity of an inner intima wall of the blood vessel on the image, on the basis of a moving average of the luminance values; and a calculation device for detecting a maximum value and a minimum value from among the luminance values respectively corresponding to a predetermined number of the pixels arranged from the base position toward a position of an outer adventitial wall on the image, and calculating the intima-media thickness on the basis of the maximum value and the minimum value.

9 Claims, 13 Drawing Sheets

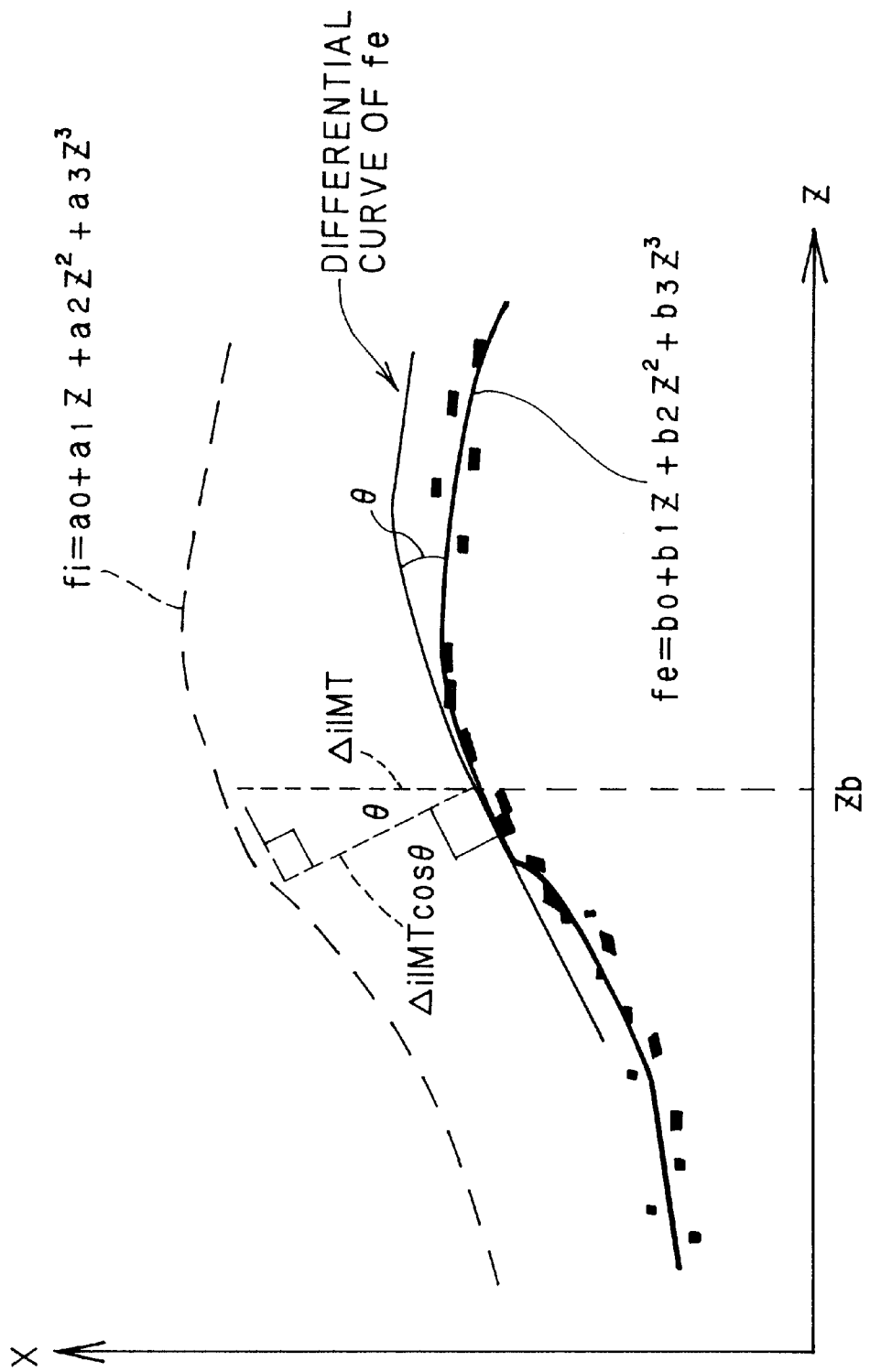

$$IMT = (PIMT + avg1IMT + avg2IMT)/3$$

INTIMA-MEDIA THICKNESS MEASURING APPARATUS AND ARTERIAL SCLEROSIS DIAGNOSING SYSTEM

BACKGROUND OF THE INVENTION

1. Field of the Invention

The present invention relates to a measuring apparatus for measuring an intima-media thickness of a carotid arteries, and an arterial sclerosis diagnosing system for diagnosing arterial sclerosis using the results of measurement performed by the measuring apparatus.

2. Description of the Related Art

In the past, arterial sclerosis has been diagnosed by examining a change in a vascular lumen through arteriography. However, since this method requires administration of a contrast medium or x-radiation, it cannot be implemented readily. Moreover, it takes much time for diagnosis.

In recent years, the possibility of adopting a composite thickness of the tunica intima and media, i.e., an intima-media thickness (hereinafter referred to as an "IMT") of a carotid arteries as an index of judgment of arterial sclerosis has been studied in the world. Above all, a method of imaging a carotid artery using an ultrasound system, and measuring the IMT using an ultrasonic image for the purpose of diagnosis is attracting attention.

According to the method, images of carotid arteries can be produced relatively easily. Moreover, measurement can be achieved relatively highly precisely. A measured IMT highly correlates with the one retrieved pathologically.

However, according to the foregoing conventional method, calipers are used to measure an IMT using an ultrasonic image. This poses a problem in that high-precision measurement cannot be expected unless an experienced physician carries out measurement by taking much time. Even a physician who has gotten accustomed to the measurement requires, for example, time ranging from 20 minutes to 30 minutes. Not only that it takes too much time for measurement but also the measurement is accompanied by an error dependent on the technical level of a measuring physician.

For solving the above problems, computerized methods of automatically measuring an IMT using an ultrasonic image have been proposed in some countries. However, these methods require coupling of a computer to a conventional ultrasound system. If any of the methods were implemented in an actual system, the system would be quite expensive. The prices of conventional ultrasound systems are generally as high as several tens of million yen. Any conventional ultrasound system cannot therefore be readily installed at any clinical site from the viewpoint of the price.

Moreover, a video output terminal through which an analog signal is input is generally used to capture images produced by an ultrasound system into a computer. Even when an ultrasound system reads an image as digital data, the data must be converted into an analog signal and then sent to a computer. Moreover, the computer must convert the analog video signal representing the image into digital data using video capture software or the like. According to the conventional method, therefore, deterioration in image quality cannot be avoided. This deterioration in image quality causes difficulty or errors in measuring an IMT, because measurement of an IMT requires accurate measurement in the order of 0.1 mm. Therefore, efforts must be made not to deteriorate image quality as much as possible.

In a conventional IMT measuring system based on a computer, advanced image processing is carried out in consideration of deterioration in image quality. The price of software to be installed is therefore as high as several millions yen.

SUMMARY OF THE INVENTION

An object of the present invention is to provide an intimamedia thickness measuring apparatus capable of accurately measuring an IMT using ultrasonic images of carotid arteries despite a relatively inexpensive and simple configuration, and to provide an arterial sclerosis diagnosing system capable of properly diagnosing arterial sclerosis according to measured data.

The above-stated object can be achieved by the measuring apparatus in accordance with the present invention. This measuring apparatus can accurately measure an intima-media thickness of a blood vessel. The measuring apparatus includes: an ultrasound device for outputting a digital image data representing an image of the blood vessel produced by scanning the blood vessel with an ultrasound; and a data analyzing device for receiving the output digital image data and calculating the intima-media thickness of the blood vessel according to the received digital image data.

Further, the digital image data includes a plurality of luminance values each corresponding to respective one of a plurality of pixels of the image. The data analyzing device includes: a setting device for setting a base position between a center of the blood vessel and a position in a vicinity of an inner intimal wall of the blood vessel on the image, on the basis of a moving average of the luminance values; and a calculation device for detecting a maximum value and a minimum value from among the luminance values respectively corresponding to a predetermined number of the pixels arranged from the base position toward a position of an outer adventitial wall on the image, and calculating the intima-media thickness on the basis of the maximum value and the minimum value.

In this measuring apparatus, the ultrasound device scans the blood vessel. Then, for example, an image of a section of the blood vessel including sections of the intima, media and adventitia is obtained. The ultrasound device further produces digital image data representing this image, and outputs the digital image data to the data analyzing device.

The intima, media and adventitia can be discriminated on the basis of changes in density of tissue thereof. A change in density of tissue of the blood vessel appears as a change of luminance values in the digital image data. The data analyzing device detects and calculates the intima-media thickness on the basis of the changes of luminance values in the digital image data.

In the data analyzing device, a certain part of the image of the blood vessel including parts of the intima, media and adventitia is extracted as a target part. For example, the target part is a line of pixels extending along the radius of the blood vessel from a side near the center of the blood vessel toward an outside of the outer adventitial wall of the blood vessel on the image, traversing the intima, media and adventitia.

The setting device next calculates a moving average of the luminance values in the target part, and sets a base position between the center of the blood vessel and the position in the vicinity of the inner intima wall of the blood vessel within the target part on the image, on the basis of the moving average.

The calculation device next detects the maximum value and the minimum value from among the luminance values respectively corresponding to the predetermined number of the pixels arranged from the base position toward a position of the outer adventitial wall in the target part on the image.

The calculation device next calculates the position of the inner intimal wall and the position of the inner adventitial wall on the basis of the maximum value and the minimum value, and further calculates the intima-media thickness, which is the difference between the position of the inner intimal wall and the position of the inner adventitial wall.

In this manner, on the basis of the changes of the luminance values of the image, the positions of the inner intimal wall and the inner adventitial wall can be easily and accurately detected, so that the intima-media thickness accurately and quickly measured.

In the measuring apparatus, the setting device may include a base position setting device for setting a position at which an increasing rate of the luminance values exceeds a predetermined rate as the base position. A change of the luminance value is relatively large in a region corresponding to the intima, media and adventitia, because a change of tissue in density is large. In a region between the center of the blood vessel and the vicinity of the inner intimal wall, a change of the luminance value is relatively small, because there is almost no image corresponding to the section of tissue in this region except for the vicinity of the inner intimal wall. The base position setting device traces the target part (line of pixels) from a side of the center of the blood vessel toward the outer adventitial wall, while determining whether or not the increasing rate of the luminance values exceeds the predetermined rate. When the increasing rate of the luminance values exceeds the predetermined rate, the base position setting device sets the present tracing position as the base position. This position indicates a position that a large change of the luminance values appears. This means that the tissue in density of the blood vessel may largely changes from this position. Therefore, it may be determined that the intima, media and adventitia are located from this position. Consequently, the region in which the intima and media are located can be easily restricted.

Further, in the measuring apparatus, the thickness calculation device may includes: a first detection device for detecting a first maximum value from among the luminance values respectively corresponding to the predetermined number of the pixels arranged from the base position toward the position of the outer adventitial wall on the image, and detecting a position of the pixel corresponding to the first maximum value as a first position; a second detection device for detecting a second maximum value from among the luminance values respectively corresponding to the pixels arranged between the base position and the first position, and detecting a position of the pixel corresponding to the second maximum value as a second position; a third detection device for detecting a third position at which a change of the luminance values is changed over from a decrease to a increase by scanning the change of the luminance values from the second position toward the center of the blood vessel, and setting the third position as a position of an inner intimal wall of the blood vessel on the image; a fourth detection device for detecting a first minimum value from among the luminance values respectively corresponding to the pixels arranged between the first position and the second position, and detecting a position of the pixel corresponding to the first minimum value as a fourth position; a first calculation device for calculating a position of an inner adventitial wall by using a value representing the first position and a value representing the fourth position; and a second calculation device for calculating a difference between a value representing the position of an inner intrimal wall and a value representing the position of an inner adventitial wall, thereby obtaining the intima-media thickness.

In this thickness calculation device, the first detection device detects the first maximum value from among the luminance values respectively corresponding to the predetermined number of the pixels arranged from the base position toward the position of the outer adventitial wall on the image, and further detects the position of the pixel corresponding to the first maximum value as a first position. This position corresponds to the position of the adventitia.

The second detection device next detects the second maximum value from among the luminance values respectively corresponding to the pixels arranged between the base position and the first position, and further detects the position of the pixel corresponding to the second maximum value as a second position. This position corresponds to the position of the intima.

The third detection device next detects a third position at which a change of the luminance values is changed over from decrease to increase by scanning the change of the luminance values from the second position toward the center of the blood vessel. This position corresponds to the position of the inner intimal wall.

The fourth detection device next detects the first minimum value from among the luminance values respectively corresponding to the pixels arranged between the first position and the second position, and further detects the position of the pixel corresponding to the first minimum value as a fourth position. Then, the first calculation device calculates the position of the inner adventitial wall by using a value representing the first position and a value representing the fourth position.

The second calculation device next calculates a difference between a value representing the position of an inner intrimal wall and a value representing the position of an inner adventitial wall, thereby obtaining the intima-media thickness.

In this thickness calculation device, the first calculation device may calculate the position of the inner adventitial wall according to an equation:

$$Xb=(MPX-MX)/2+MX,$$

where the Xb is a value representing the position of the inner adventitial wall, the MPX is a value representing the first position, the MX is a value representing the fourth position.

It is to hard to specify the position of the inner adventitial wall because a change in tissular density between the media and adventitial is not large. However, according to this first calculation device, the position of the inner adventitial wall can be easily specified by using such a simple equation. Therefore, it is not needed to use an expensive ultrasound system.

Furthermore, in the measuring apparatus, the thickness calculation device may includes: a first collecting device for collecting a plurality of values each representing the position of the inner intimal wall of the blood vessel on the image, by carrying out a detection of the position of the inner intimal wall a plurality of times at a plurality of different detecting positions, while shifting the detection position in a direction along an axis of the blood vessel; a third calculation device for calculating a first regression curve by using the plurality of values collected by the first collection device; a second collecting device for collecting a plurality of values each representing the position of the inner adventitial wall of the blood vessel on the image, by carrying out a detection of the position of the inner adventitial wall a plurality of times on a plurality of different detecting positions, while shifting the detection position in a direction along an axis of the blood vessel; a fourth calculation device for calculating a second regression curve by using the plurality of values collected by the second collection device; a fifth calculation device for calculating a plurality of thickness values respectively representing the intima-media thickness at the plurality of difference detection positions, on the basis of differences between the first regression curve and the second regression curve; and an average device for calculating an average of a maximum value among the plurality of thickness values and at least two of the plurality of thickness values except for the maximum value.

In this thickness calculation device, the first collecting device collects a plurality of values each representing the position of the inner intimal wall, while shifting the detection position in the direction along the axis of the blood vessel. The third calculation device next calculates a first regression curve by using the collected values. Similarly, the second collecting device collects a plurality of values each representing the position of the inner adventitial wall, while shifting the detection position in the direction along the axis of the blood vessel. The fourth calculation device next calculates a second regression curve by using the collected values. The fifth calculation device next calculates a plurality of thickness values respectively representing the intima-media thickness at the plurality of difference detection positions, on the basis of differences between the first regression curve and the second regression curve. The average device calculates the average of the maximum value among the plurality of thickness values and at least two of the plurality of thickness values except for the maximum value.

In this thickness calculation device, the intima-media thickness is calculated using data detected from the plurality of detection positions. Therefore, if the blood vessel is tortuous, the intima-media thickness can be accurately measured. Further, since the intima-media thickness is finally determined by averaging the maximum value of the thickness values and at least two of the thickness values, it can be prevented an error or variation of the result of the calculation.

Moreover, in the thickness calculation device, the fifth calculation device may calculate at least one of the plurality of thickness values by using a tangent of at least either one of the first regression curve and the second regression curve.

Moreover, in the measuring apparatus, the ultrasound device may output a plurality of digital image data. Further, the data analyzing device may calculate the intima-media thickness of the blood vessel according to the plurality of digital image data. The plurality of image data may be obtained by scanning a part of the blood vessel with the ultrasound while changing a position from which the ultrasound is radiated. Therefore, the intima-media thickness can be accurately measured.

Moreover, a storage device and an evaluation table generating device may be added to the measuring apparatus. The storage device is a device for storing data representing intima-media thickness with respect to a plurality of examinees or patients. The evaluation table generating device is a device for generating an evaluation table in which data indicating averages and distributions of the intima-media thickness for each age of the examinees or patients are described. By adding these devices to the measuring apparatus, efficient and proper diagnosis of arterial sclerosis can be easily done on the basis of reliable clinical data.

Moreover, the ultrasound device and the data analyzing device may be optically connected by an optically coupled device. Therefore, safety for medical use is ensured.

The nature, utility, and further feature of this invention will be more clearly apparent from the following detailed description with respect to preferred embodiments of the invention when read in conjunction with the accompanying drawings briefly described below.

BRIEF DESCRIPTION OF THE DRAWINGS

FIG. 10 shows a regression curve to be plotted in the course of measuring an IMT in accordance with the present invention, and a differential curve of the repression curve, and indicating a method of correcting a measured value using the differential curve;

DETAILED DESCRIPTION OF THE PREFERRED EMBODIMENTS

Referring to the accompanying drawings, an embodiment of the present invention will be described.

1. System Configuration

Figure 1:
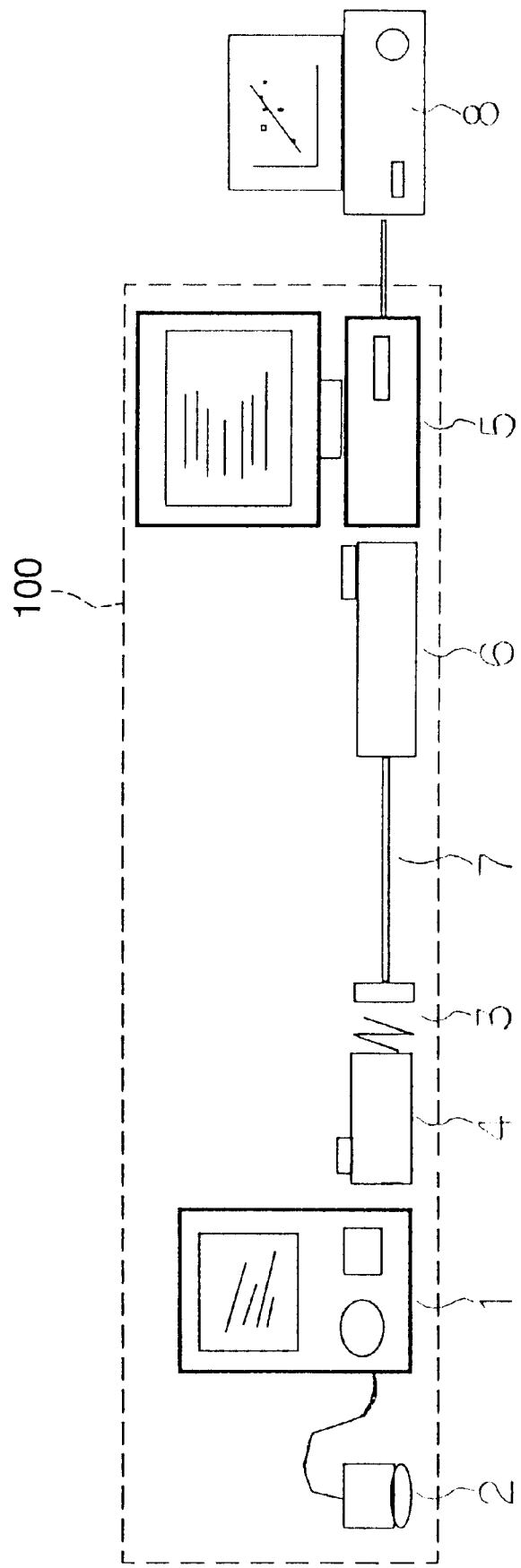
FIG. 1 is an illustration showing a configuration of an arterial sclerosis diagnosing system as an embodiment in accordance with the present invention.

FIG. 1 shows a configuration of a measuring system 100 as an embodiment in accordance with the present invention. This system 100 can measure an IMT of a carotid artery accurately and in easy operations. The measuring system 100 includes a compact linear ultrasound apparatus 1 and a linear probe 2. The compact linear ultrasound apparatus 1 is as large as a personal computer in size.

This apparatus 1 adopts a linear probe 2 offering a frequency ranging from 7.5 MHz to 10 MHz. Such a frequency range is based on the following viewpoint. The higher a frequency offered by an ultrasonic probe is, the higher a distance resolution is. However, when the frequency is too high, ultrasonic waves cannot reach a deep region because of a large decay thereof. In consideration of the location of a carotid artery, the aforementioned frequency range is appropriate. In addition, the distance resolution can be set to about 0.1 mm on the assumption that an acoustic velocity is 1,500 m/s. This is because a limit value of the distance resolution is a half of a wavelength attained at the frequency offered by the probe, in principle.

The measuring system 100 further includes a digital output board 4. This board 4 is incorporated in the ultrasound apparatus 1. The digital output board 4 can output an image to be read as digital data by the probe 2 as the digital data. That is, the ultrasound apparatus 1 reads an image through the probe 2 as digital data, and then, the digital output board 4 outputs this data as digital data. Converting the read data into an analog signal is not performed.

Furthermore, the digital output board 4 is photo-isolated by a photo-isolator 3. Since a personal computer 5 to be described later is photo-isolated from the ultrasound apparatus 1 by the photo-isolator 3, safety for medical use is ensured.

The measuring system 100 still further includes the personal computer 5. The personal computer 5 is a general-purpose personal computer that runs on an operating system such as Windows 95. The personal computer 5 includes a memory that is large enough to process image data. Moreover, the personal computer 5 includes a hard disk in which IMT measuring software, evaluating and diagnosing software, database software, printing software, and digital image capturing software are installed.

Moreover, the personal computer 5 includes a PCI (Peripheral Component Interconnect) bus over which a digital input board 6 is connected. The digital input board 6 is connected to the digital output board 4 incorporated in the ultrasound apparatus 1 via the photo-isolator 3 and a connection cable 7. The digital input board 6 inputs digital data output from the digital output board 4. This digital data is stored in a memory in the personal computer 5. In this system, a printer 8 may be connected as an option to the personal computer 5. When the system is thus configured, the results of measurement can be printed out.

II. IMT Measurement

Next, a description will be made of the principles of IMT measurement to be performed using the foregoing system.

Figure 2:
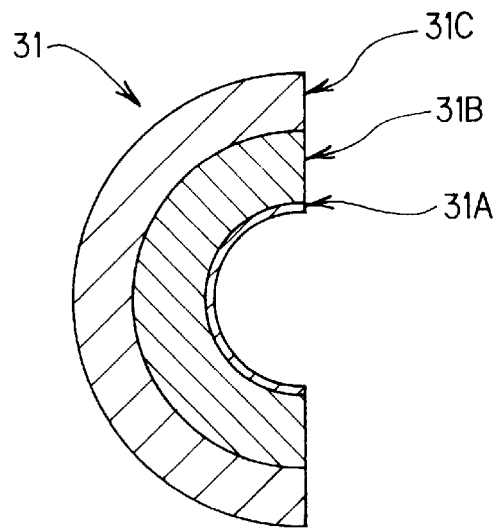
FIG. 2 is a sectional view showing the structure of an artery.
Figure 3:
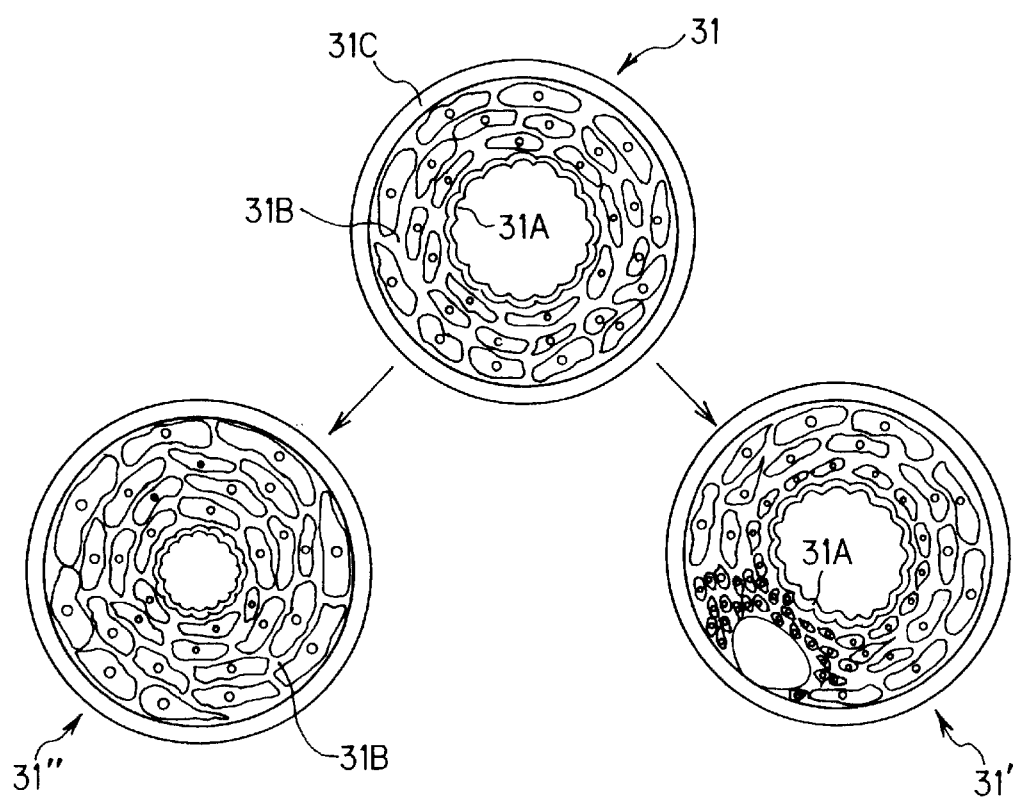
FIG. 3 is a sectional view showing a normal artery, an abnormal artery whose media is thicken because of hypertension, and another abnormal artery whose intima is thicken because of arterial sclerosis.

As shown in FIG. 2, an artery 31 is divided into three layers of the tunica intima 31A, media 31B, and adventitia 31C from inside. It is known that the tunica intima 31A or media 31 B thickens due to a lesion. For example, as shown by the numeral 31' in FIG. 3, arterial sclerosis causes the intima 31A to thicken. Further, as shown by the numeral 31" in FIG.3 hypertention causes the media 31B to thicken. The symptoms of the respective diseases can therefore be evaluated by measuring the thickness of the intima 31A or media 31B.

Figure 4:
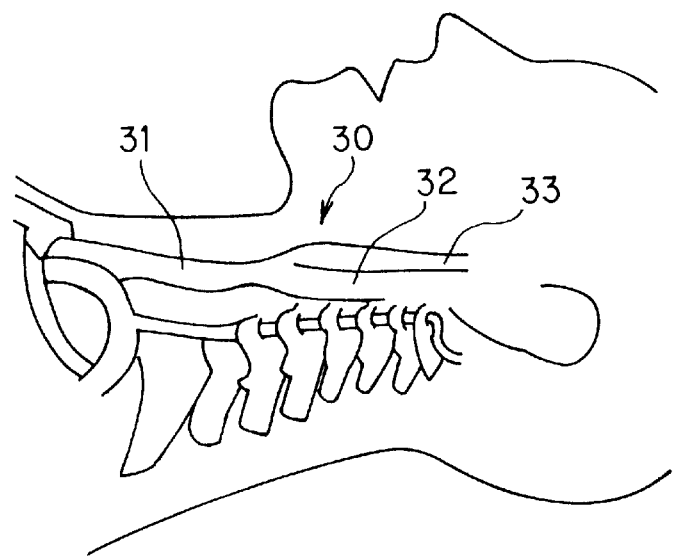
FIG. 4 is an illustration for explaining measured positions of carotid arteries.

The carotid artery 30, as shown in FIG. 4, are adopted as an object of measurement. This is because the diameter of the carotid artery 30 located at a 2-to-3 cm subcutaneous position is about 5 mm, and ultrasonic waves therefore readily reach the carotid arteries. Moreover, the common carotid artery 31 is, as shown in FIG. 4, bifurcated into the internal carotid artery 32 and the external carotid artery 33 near the neck. For measuring an IMT, the probe 2 is placed at the bifurcated region of the common carotid artery 31 and moved longitudinally toward the common carotid artery 31 for measurement.

Figure 5:
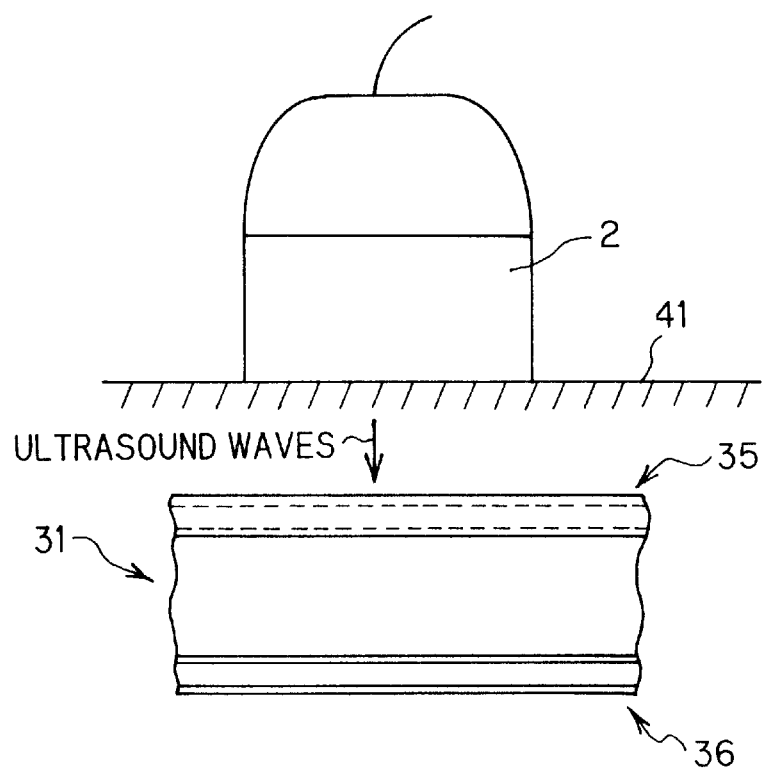
FIG. 5 is an illustration for explaining a positional relationship between a ultrasound probe and a carotid artery.

The probe 2 is used to emit ultrasonic waves to the common carotid artery 31. Ultrasonic waves are reflected from a region whose tissue undergoes a change in density. The ultrasonic waves are therefore reflected more greatly from the region of the intima or adventitia. FIG. 5 shows an exemplary ultrasonic image produced in this situation. As shown in FIG. 5, the region reflecting ultrasonic waves more greatly appears as a high-luminance area in an ultrasonic image on the display screen of the ultrasound apparatus 1. Therefore, a change in luminance is measured in a direction in which a blood vessel is traversed, whereby the IMT can be measured.

A change in density of tissue appears a change in luminance of the displayed image. However, it is very hard work to visually measure a change in luminance and measure the IMT with precision permitting an error of 0.1 mm. In particular, blood vessels are not straight but microscopically tortuous. It is very hard to discern a direction perpendicular to a vascular wall. Consequently, precise measurement cannot be achieved by the visual observation.

In this embodiment, image data read as a digital data by the ultrasound apparatus 1 is captured in the form of digital data into the personal computer 5. A peak value of luminance values is detected through numerical analysis, whereby a change in luminance is measured. Based on the results of measuring the change in luminance, the locations of the intimal and adventitial walls in a radial direction of a blood vessel are detected at a plurality of positions in a longitudinal direction of a blood vessel. A tangent is searched for relative to a regression curve indicating the correlation between the locations of the intimal and adventitial walls. The locations of the intimal and adventitial walls are expressed as functions of the positions in the longitudinal direction of the blood vessel. Consequently, the IMT can be measured highly precisely in the direction perpendicular to a vascular wall. A description will be made of the principles of measuring an IMT in accordance with this embodiment. For the description, a step of calculating the locations of the intimal and adventitial walls and a step of calculating IMT using a repression curve expressing the correlation between the locations of the intimal and adventitial walls will be explained below.

II-a. Detection of Locations of Intimal Wall and Adventitial Wall

The probe 2 is placed on the skin 41 as shown in FIG. 5. A vascular wall 35 near the probe emitting ultrasonic waves (hereinafter referred to as a "near wall 35") and a vascular wall 36 away therefrom (hereinafter referred to as a "far wall 36") can be observed. However, the near wall 35 may often be imaged unclearly because of multi-reflection of the ultrasonic waves or the like. In this embodiment, therefore, the far wall 36 is regarded as a region of IMT to be measured.

Figure 6A:
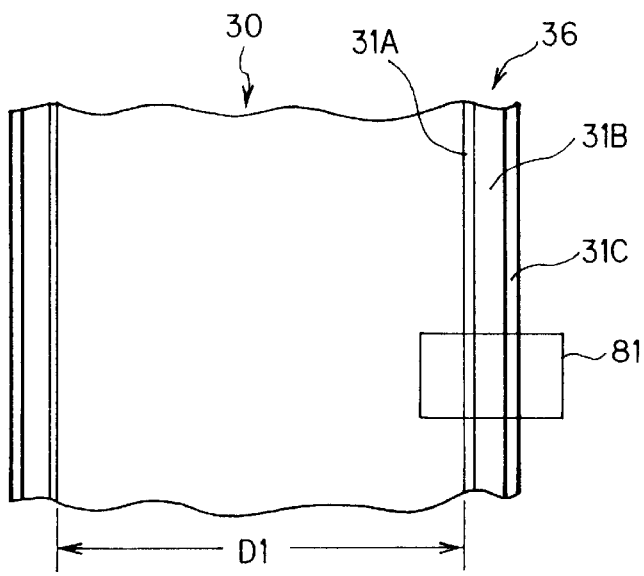
FIG. 6A is an illustration showing an example of actual images used to measure an IMT.

FIG. 6A shows an example of images of the carotid artery 31. An image shown in FIG. 6A appears on the display of the personal computer 5 as a result of inputting an image read by the ultrasound apparatus 1 as digital data to the personal computer 5.

For measuring a thickness of intima 31A and a thickness of media 31B, it is required to clearly discern the location of the inner intimal wall near the center of a blood vessel, the location of the border between the intima 31A and media 31B (the outer intimal wall of the inner medial wall), and the location of the border between the media 31B and adventitia 31C (the outer medial wall or the inner adventitial wall). However, since a change in tissular density of the intima 31A or media 31B is not very large, the location of the border between the intima 31A and media 31B cannot be specified in an ultrasonic image. In this embodiment, therefore, an IMT that is a composite thickness of the intima 31A and media 31B is measured by calculating a difference between the location of the inner intimal wall and the location of the inner adventitial wall.

An area employed for measurement may be chosen arbitrarily by a measuring physician. For example, a measuring physician handles a mouse connected to the personal computer 5 to move a mark to a desired position as shown in FIG. 6A. The mark is referred to as a template 81 and appearing on the display of the personal computer 5. A mouse button is then clicked in order to specify a measured position.

Figure 6B:
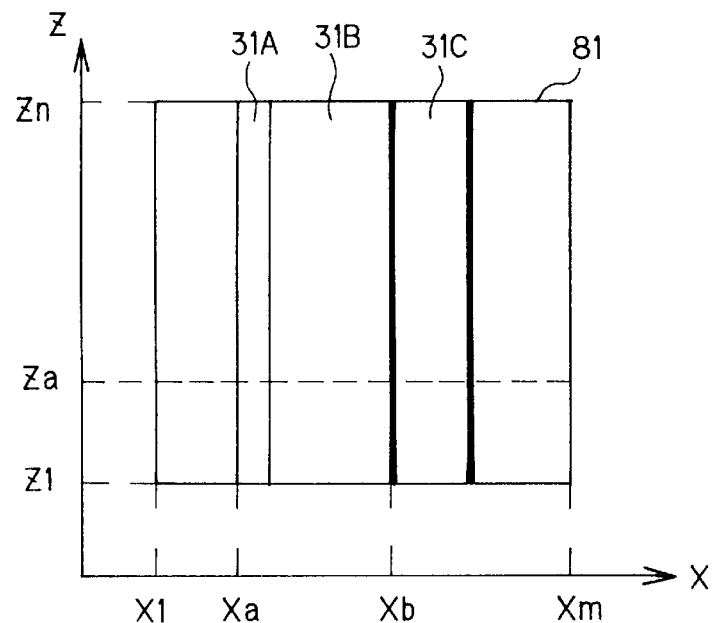
FIG. 6B is an illustration showing a measured area in the example shown in FIG. 6A.

A change in luminance in the radial direction D1 of a blood vessel is measured based on image data of an area cut with the template 81. FIG. 6B is a chart illustratively showing the image data cut with the template 81 shown in FIG. 6C. For measurement, the image data is, as shown in FIG. 6B, dealt with by regarding the radial direction D1 of a blood vessel as the X-axis direction and the longitudinal direction thereof as the Z-axis direction. The size of image data varies depending on the size of the template 81. For example, the template 81 has a size covering m pixels in the X-axis direction and n pixels in the Z-axis direction. In this case, image data having a size of m pixels by n pixels can be acquired. Measurement is carried out for each pixels as follows. The pixel (X1, Z1) is firstly measured. The pixel located next to the pixel (X1, Z1) is secondly measured. In this manner, the measurement is carried out in the direction along to the X-axis up to the pixel (Xm, Z1). Such a measurement is repeatedly carried out for each rows Z1 through Zn. In such a measurement, luminance values corresponding to respective pixels is obtained. As a result, changes of luminance values are measured.

Figure 6C:
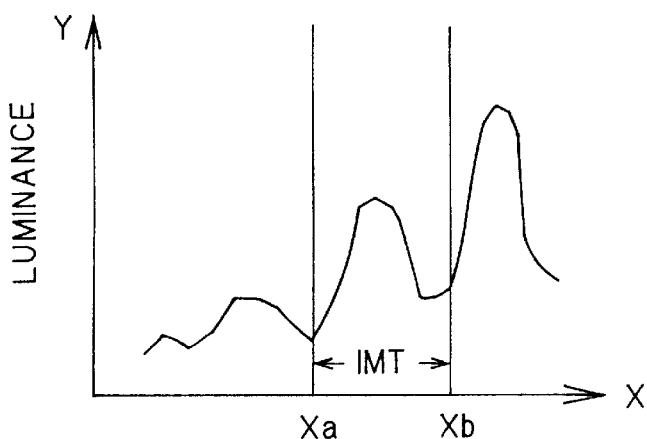
FIG. 6C shows a change in luminance at a predetermined position within the measured area shown in FIG. 6B.

FIG. 6C shows an example of the results of the above measurement. FIG. 6C shows the results of measuring a luminance value in image data composed of m pixels arranged along the X axis on the a-th row of pixels read as a coordinate Za in FIG. 6B. In FIG. 6C, a change in luminance value is read on the Y axis. As seen from FIG. 6C, a curve indicating luminance values has several peaks. The largest peak value is observed at a point indicating a position on the adventitia where the highest tissular density is detected. A second largest peak value is observed at a point indicating a position on the intima where the second highest tissular density is detected. Points Xa and Xb from which the curve rises to the peak values are regarded as points indicating the locations of the inner intimal and adventitial walls. In this embodiment, the point Xb from which the curve rises up to the largest peak value which indicates a position on the adventitia is regarded as the location of the inner adventitial wall. The point Xa from which the curve rises up to the second largest peak value which indicates a position on the intima is regarded as the location of the inner intimal wall.

Figure 7:
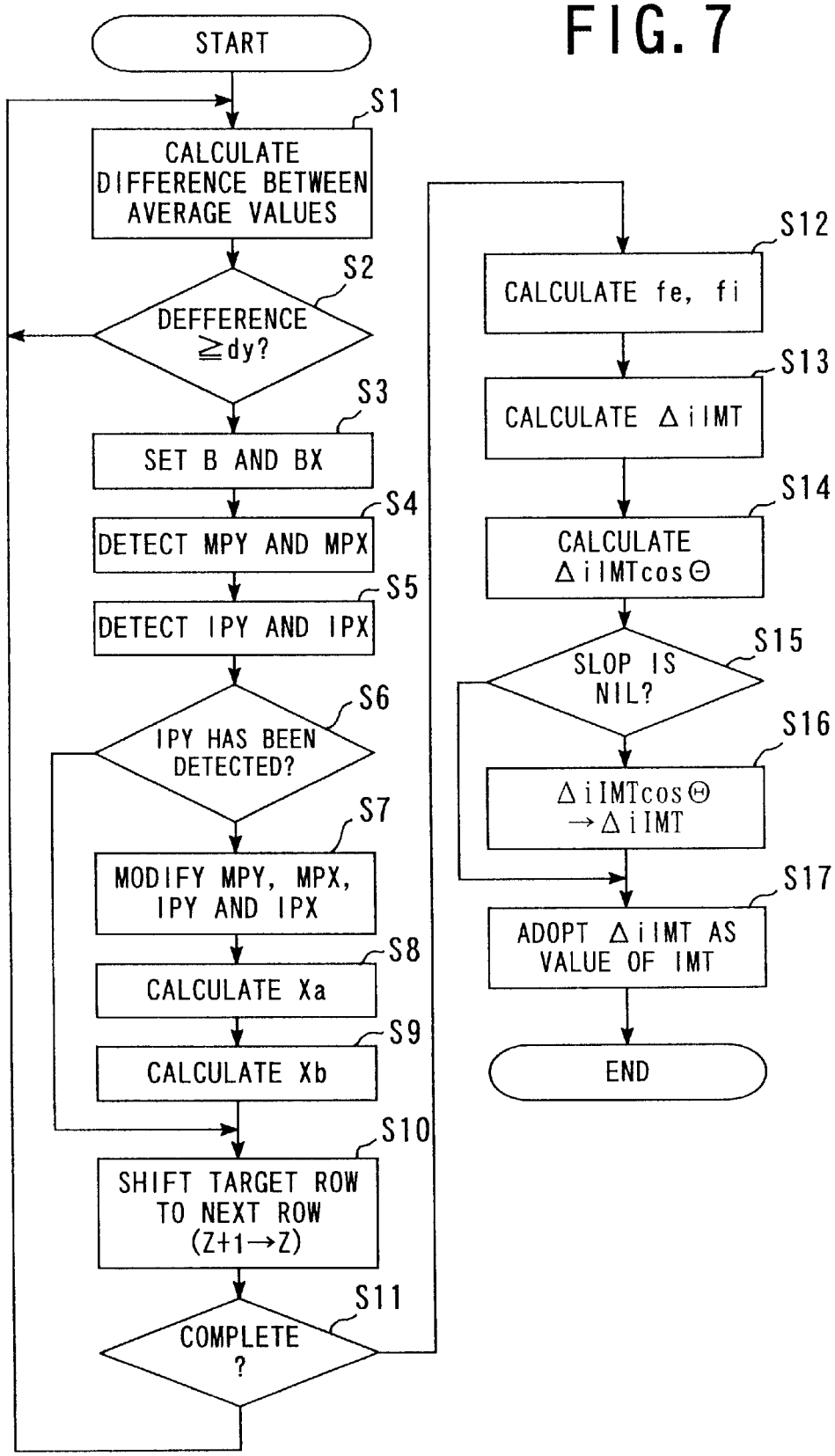
FIG. 7 is a flowchart describing an algorithm for measuring an IMT in accordance with the present invention.

Next, an exemplary algorithm for calculating the location of the inner intimal wall and the location of the inner adventitial wall will be described in conjunction with the flowchart of FIG. 7 and the graphs of FIG. 8 and FIG. 9.

Figure 8:
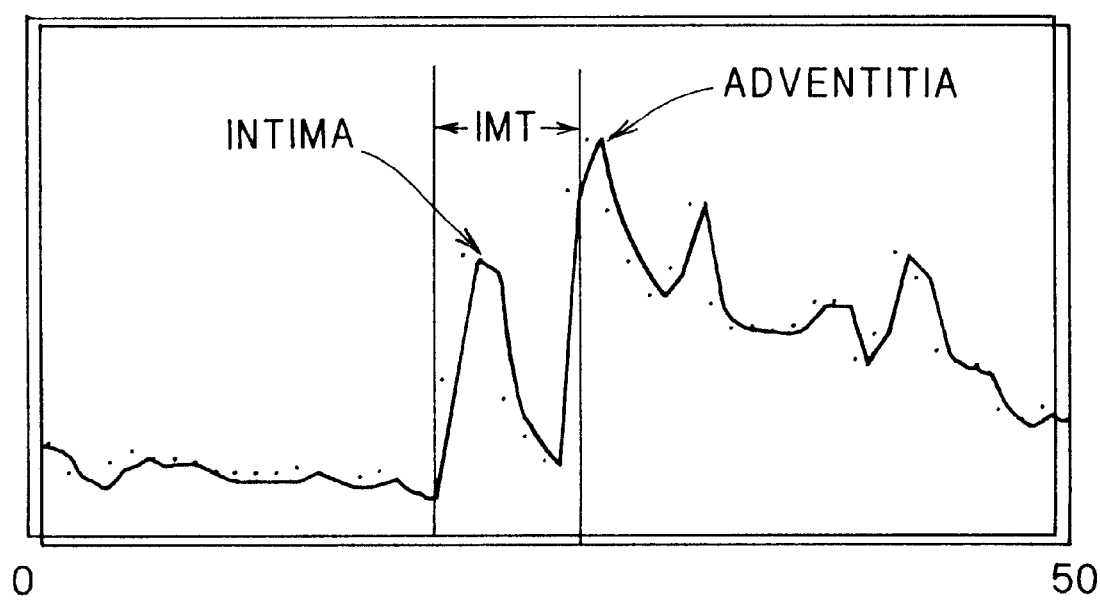
FIG. 8 shows values showing a change in luminance that are actually measured with a system in accordance with the present invention.

Incidentally, in FIG. 8 and FIG. 9, the axis of abscissas indicates positions of pixels arranged along the X axis from a start position of measurement. The axis of ordinates indicate luminance values observed in an image. Points are plotted which are located on extensions of the positions of pixels and indicating the luminance values observed in an image. In FIG. 8 and FIG. 9A to FIG. 9E, the Y axis indicates luminance values.

For measurement, for example, the template 81 is moved to a desired position. The position is specified as a measured position by clicking a mouse butt on. Measurement start is selected from a command menu or the like and a mouse button is clicked. This causes measurement to start. Image data composed of m pixels ranging from the first pixel to the m-th pixel is extracted. The m pixels are arranged along the X axis on the first row of pixels read on the Z axis within the template 81. FIG. 8 is a graph drawn by plotting points of luminance values observed in the thus extracted image data. In FIG. 8, straight lines are not fitted on the plotted points for a better understanding. Moreover, data composed of 50 pixels arranged along the X axis is extracted as an example.

Figure 9A:
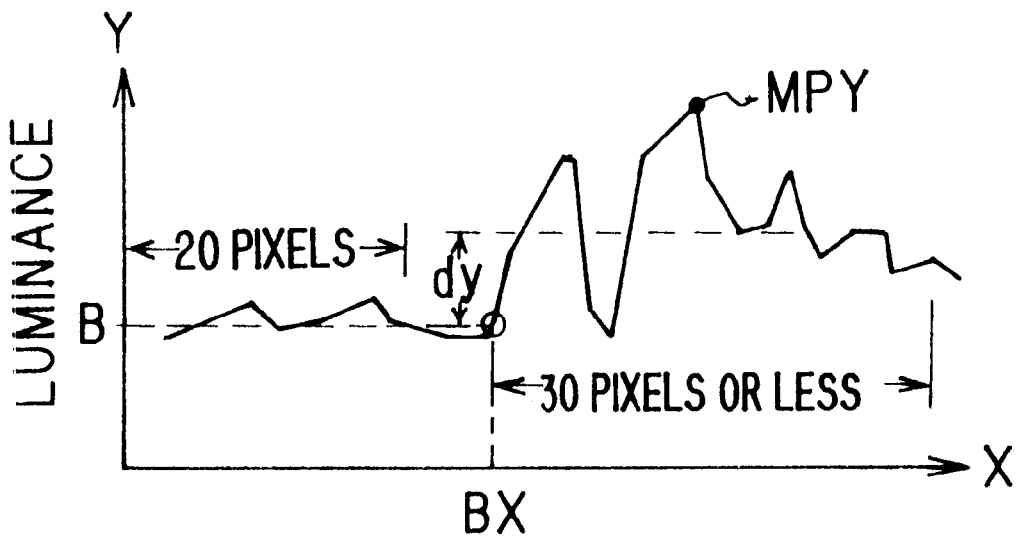
FIGS. 9A to 9E show a variety of conditions of changes in luminance obtained in an IMT measurement.

Next, a moving average value of luminance values is calculated in units of 20 pixels from the start position of measurement (the first pixel read as the coordinate X1 in FIG. 6B). A difference of the latest average value from the previous average value, Δ, is calculated (step S1). It is then determined whether the difference exceeds a predetermined value dy (step S2). The difference may fall below the predetermined value dy (in the negative at step S2). In this case, a moving average of luminance values of the next 20 pixels is calculated, and a difference from the previous average is calculated (step S1). However, the difference may exceed the predetermined value dy as shown in FIG. 9A (in the affirmative at step S2). In this case, the previous average value is stored as a base B for low luminance. The position of the leading pixel out of pixels whose luminance values are averaged this time is stored as a base position BX (step S3).

Figure 9B:
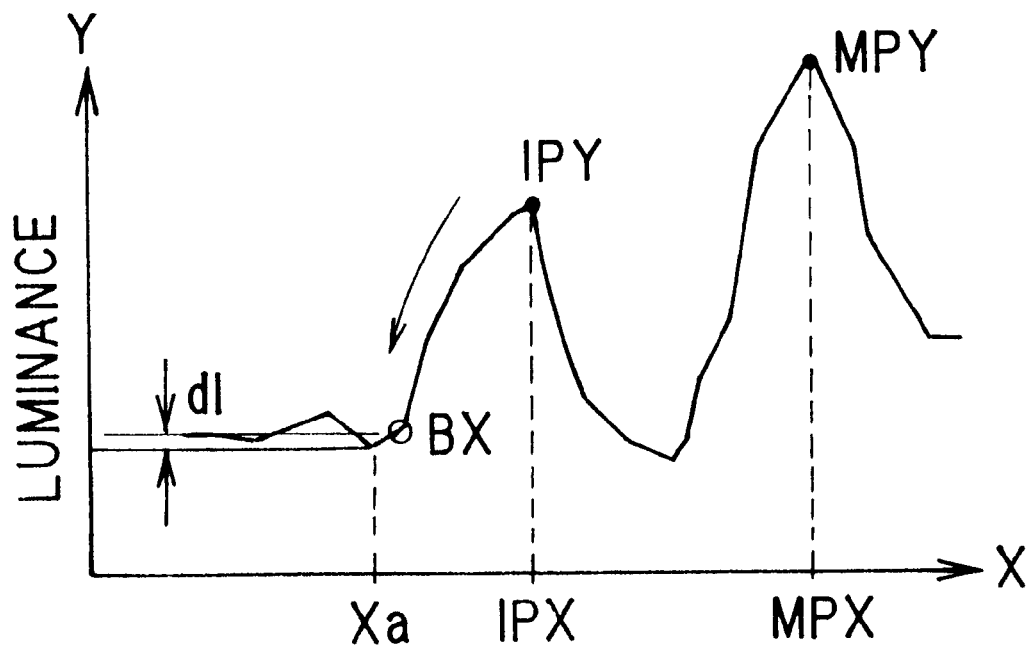

Thereafter, a luminance value of each pixel out of 30 pixels or less from the pixel at the base position BX is compared with that of a subsequent pixel. The largest peak value MPY out of luminance values shown in FIG. 9A and FIG. 9B is detected, and the position MPX of the pixel having the largest luminance value is detected (step S4). The largest peak value MPY is the luminance value stemming from reflection from the adventitia 31C. The position MPX indicates the location of the adventitia 31C.

After the peak value MPY and peak position MPX are detected, a peak value IPY and a peak position IPX shown in FIG. 9B are detected by comparing one luminance value with a subsequent one from the luminance value at the peak position MPX to the luminance value at the base position BX (step S5). The peak value IPY is the luminance value obtained by stemming from reflection of ultrasonic waves from the intima 31A. The position IPX indicates the location of the intima 31A. The foregoing detection is carried on until the luminance value at the base position BX is compared with the previous one.

Figure 9C:
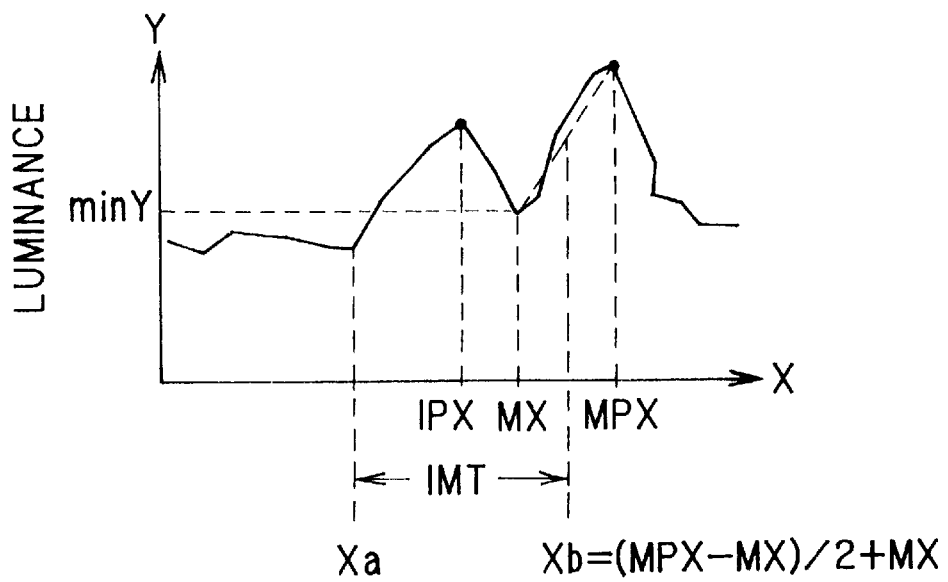
Figure 9D:
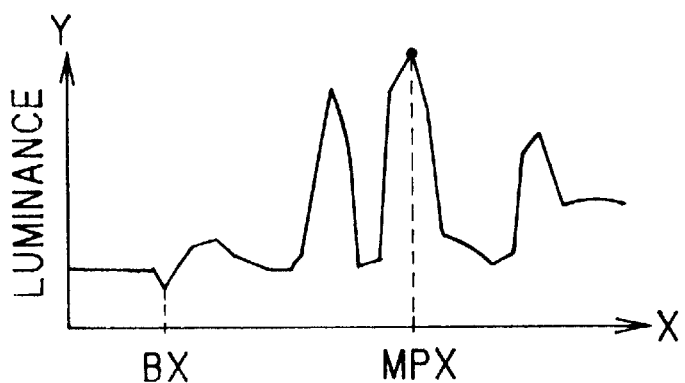
Figure 9E:
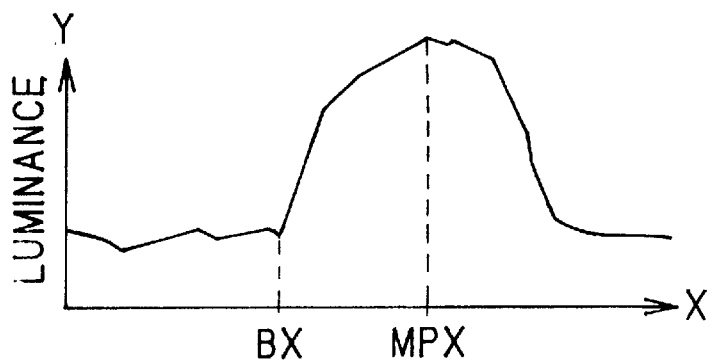

However, when a noise appears in an image, the peak value IPY indicating the location of the intima 31A may not be detected as shown in FIG. 9E. After the detection is completed up to the base position BX, it is determined whether the peak value IPY has been detected (step S6). If the peak value has not been detected, it is determined that measurement is disabled, and control is passed to processing of the next row of pixels (in the affirmative at step S6 to step S10). Moreover, even if the peak value IPY has been detected, a plurality of peak values IPY may be detected as shown in FIG. 9D. In this case, the peak value that is a luminance value at the first position from the base position BX is the peak value indicating the location of the intima. The peak value that is a luminance value at the second position from the base position BX is the peak value indicating the location of the adventitia. If necessary, the peak values IPY and MPY and the pixel positions IPX and MPX are modified (step S7).

Next, a position at which a decreasing luminance value starts increasing is detected from the position IPX indicating the location of the intima 31A towards the base position BX. The position or a position at which a decrease in the luminance value becomes equal to or smaller than dI is, as shown in FIG. 9B, regarded as a position Xa (step S8). The position Xa is a position at which the polygonal line rises and which is thought to indicate the location of the inner intimal wall. According to the present invention, the location Xa of the inner intimal wall can be accurately detected based on a change in luminance value.

Thereafter, the location of the inner adventitial wall is calculated. The location of the inner adventitial wall is indicated by a position from which the polygonal line indicating luminance values rises up to the peak value MPY. A change in tissular density occurring on the border between the tunica media and adventitial is not very large, though it is not so small as that occurring on the border between the tunica intima and media. It is therefore not easy to calculate the position at which the polygonal line rises up to the peak value MPY. In particular, a resolution of data counts in realizing a distance resolution of 0.1 mm that is realized according to this embodiment. The system of this embodiment aims to achieve a measurement of an IMT at low costs. The system therefore uses an inexpensive ultrasound system offering a poor resolution compared with an expensive ultrasound system offering a very high resolution. In this case, it is difficult to detect the border between the tunica media and adventitial on which a change in tissular density is not large. However, the system of this embodiment can overcome this difficulty by using the following manner.

According to this embodiment, as shown in FIG. 9C, assume that a minimum value observed between MPX and IPX is regarded as minY and the associated pixel position is regarded as MX. A position associated with (MPX−MX)/2+MX is regarded as a position Xb (step S9). The position Xb is the position at which the polygonal line rises, that is, which indicates the location of the inner adventitial wall. This method of calculating the location of the inner adventitial wall according to the formula is devised experientially through in-depth comparison between a plurality of data items produced by a conventional expensive ultrasound system and a plurality of data items produced by the inexpensive system in accordance with the present invention. Experiments have revealed that the method provides the location of the inner adventitial wall with precision of a level causing no problem in practice. However, according to the present invention, the method of calculating the position at which the polygonal line rises is not limited to the above method based on the formula. Alternatively, the least squares method may be adapted to data items between minY and MPY in units of several data items.

After the location of the inner adventitial wall Xb is calculated, the number of the row of pixels to be measured which is read on the Z axis is incremented by one (step S10). The foregoing processing is repeated until the location of the inner intimal wall Xa and the location of the inner adventitial wall Xb have been measured on all rows of pixels within the template 81 (in the negative at step S11 to step S1).

II-b. Locations of Intimal and Adventitial Walls

Next, a description will be made of a step of calculating an IMT according to the data items of the locations of the inner intimal wall Xa and inner adventitial wall Xb which are calculated as mentioned above.

An IMT may be calculated by merely calculating a difference between the data items of the location of the inner intimal wall and inner adventitial wall, if it is allowed to measure the IMT roughly. However, for realizing the distance resolution of 0.1 mm, the IMT must be accurately calculated with the smallest error.

According to this embodiment, changes in the locations of the inner intimal wall and inner adventitial wall relative to the Z-axis direction are expressed with regression curves fi(Z) and fc(Z) in units of a predetermined range of pixels. An IMT is calculated based on a difference between points [fi(Z0) to fi(Zc) or fe(Z0) to fe(Zc)] on the regression curves associated with each point (for example Z0 to Zc) on the Z axis indicating the range of pixels.

Moreover, the tunica intima or adventitia may, as shown in FIG. 10, be tortuous in the longitudinal direction of a blood vessel. In this case, an IMT a direction perpendicular to the wall of the tunica cannot be calculated by merely calculating a difference between the regression curves.

According to this embodiment, for improving precision in measurement, tangents of the regression curves are detected at each point. When the slope of each tangent relative to the Z axis is not nil, an IMT calculated from a difference between points on the regression curve perpendicular to tangents is adopted as a final IMT.

To be more specific, a regression curve employed in this embodiment is expressed with a cubic polynomial. The present inventor actually measured the locations Xa and Xb of the inner intimal and adventitial walls, and raised the order of a polynomial from the first order. As a result, the present inventor has found the fact that the employment of the cubic polynomial can most smoothly express changes in the locations of the inner intimal and adventitial walls.

In this embodiment, a regression function is defined for each predetermined range of pixels that is each range of 64 columns of pixels along the Z axis. 32 columns of pixels adjoining the 64 columns of pixels in a minus direction on the Z axis and 32 columns of pixels adjoining the 64 columns of pixels in a plus direction on the Z axis are added to the 64 columns of pixels. This comes to 128 columns of pixels. Based on the data in the range of 128 columns of pixels, coefficients in cubic polynomials $\Delta$ fe=$b_0+b_1Z+b_2Z^2+b_3Z^3$, fi=$a_0+a_1Z+a_2Z^2+a_3Z^3$) are calculated. For calculating the coefficients, the least squares method is adapted to the cubic polynomials. Simultaneous linear equations (four linear equations having unknowns $b_0$, $b_1$, $b_2$, $b_3$, $a_0$, $a_1$, $a_2$, and $a_3$) that constitute a characteristic equation are thus drawn out. An inverse matrix of the characteristic equation is calculated according to an algorithm referred to as sweeping. Moreover, position data of positions on the Z axis is assigned to the thus defined cubic polynomials in order to calculate the location of the inner intimal or adventitial wall. The residuals of the calculated location, and of the locations Xa and Xb of the inner intimal and adventitial walls, which are calculated by following steps ending with step S11 in FIG. 7, are evaluated. Regression curves are then defined so that the residuals will be minimized.

The foregoing processing will be described in conjunction with the flowchart of FIG. 7. Data items of the locations Xa and Xb of the inner intimal and adventitial walls are calculated (steps Si to step S11). Thereafter, the regression curves expressing changes in the data items of the locations Xa and Xb are plotted using the cubic polynomials. An inner intimal wall curve fi and an inner adventitial wall curve fe thus ensue (step S12).

Thereafter, a difference between the inner adventitial wall curve fe and inner intimal wall curve fi, ΔiIMT, is calculated on each column of pixels on the Z axis (step S13). As positions at which the inner adventitial wall curve fe and inner intimal wall curve fi are not parallel to the Z axis, the difference ΔiIMT does provide an accurate IMT. A differential curve fe' of a tangent of the inner adventitial curve fe is plotted. A component of ΔiIMT concerning a direction perpendicular to the inner adventitial wall ΔiIMTcosΘ, is calculated (step S14).

Calculating cosΘ will be described. Assuming that a cubic polynomial is fe, a tangent is expressed as Δfe. A magnitude Δ fe/1 pixel that increases by Δfe along the X axis relative to each pixel lying on the Z axis represents a slope. Assuming that the slope of the tangent is Θ, the slope of a regression curve expressed by the cubic polynomial is given as tanΘ. That is to say, tanΘ is calculated by calculating the differential of the cubic polynomial fe. CosΘ can be derived from a trigonometric function. In this embodiment, therefore, the differential of the cubic polynomial fe is calculated in order to calculate ΔiIMTcosΘ. This processing is performed on all columns of pixels lying along the Z axis. ΔiIMTcos Θ is adopted as data of a column of pixels whose tangent has a slope that is not nil (in the affirmative at step S15 to step S16). ΔiIMT that is the difference between the inner adventitial wall curve fe and inner intimal wall curve fi is adopted as measured data of a column of pixels whose tangent has a slope that is nil (in the negative at step S15). Finally, the thus selected measured data is adopted as an IMT at the position of each column of pixels (step S17).

The foregoing sequence is an IMT measuring algorithm in accordance with the present invention. This method of the present invention makes it possible to measure an IMT more accurately and easily than the conventional method using calipers. Moreover, although a conventionally adopted expensive system is not employed, measurement can be carried out highly precisely according to a simpler method.

III. Operations of System

Figure 11:
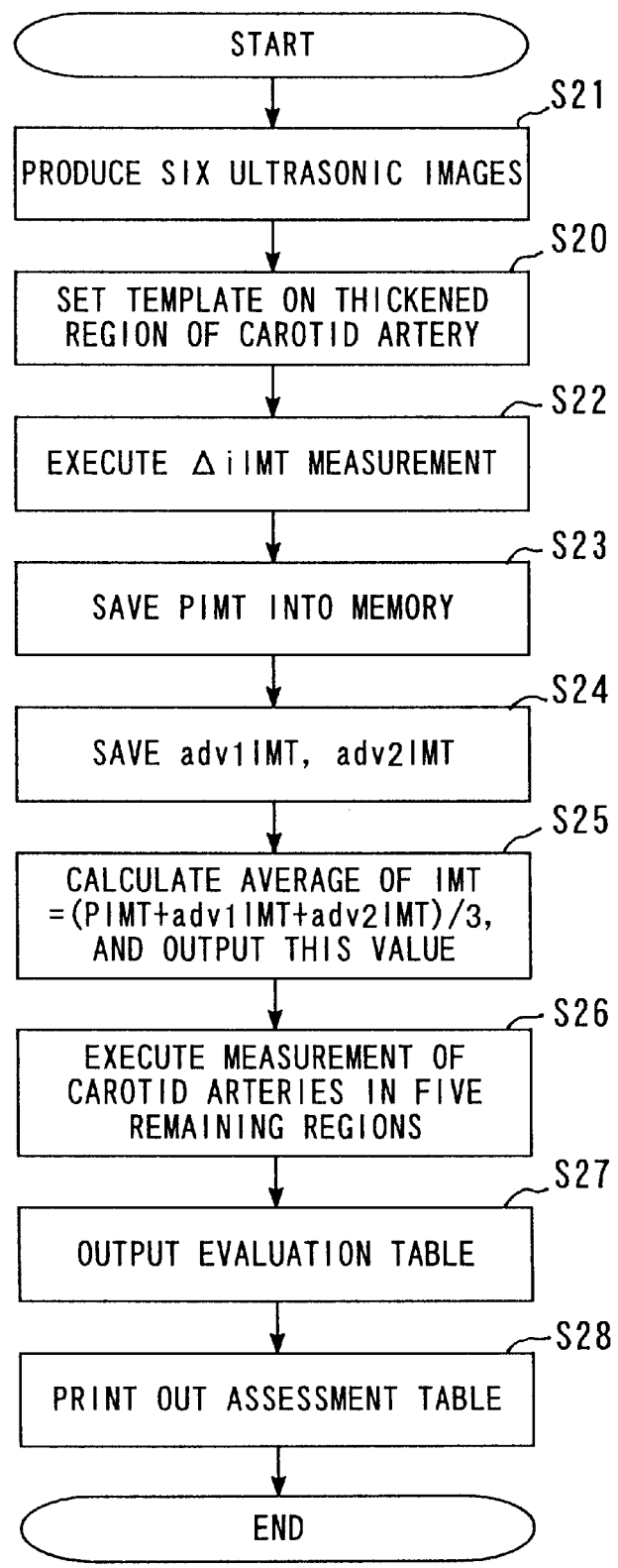
FIG. 11 is a flowchart describing actions made by the whole system shown in FIG. 1.

Next, the actual operations of the whole measuring system of this embodiment based on the foregoing principles of measurement will be described in conjunction with the flowchart of FIG. 11.

Figure 12A:
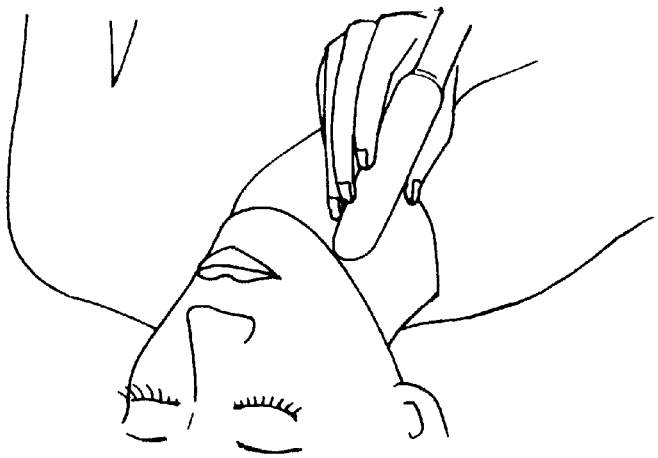
FIGS. 12A to 12C are illustrations for explaining a way to use the system in accordance with the present invention; measured regions of carotid arteries.
Figure 12B:
Figure 12C:

This embodiment adopts, as mentioned above, the method of measuring the common carotid artery 31 longitudinally. The longitudinal measurement is carried out in three directions; an anterolateral direction (FIG. 12A), lateral direction (FIG. 12B), and posterolateral direction (FIG. 12C). Since both the left and right sides of an examinee are examined, measurement is carried out in a total of six directions. In this embodiment, measurement is carried out in all the six directions. An average is calculated for each direction. Among the averages, the largest IMT value is adopted as an IMT of an object of evaluation.

First, the probe 2 is used to produce six ultrasonic images of the anterolateral, lateral, and posterolateral regions of the right and left sides of the carotid arteries. The ultrasonic images are captured as digital data into a database in the personal computer 5 (step S20 in FIG. 11).

Thereafter, a template 81 is placed so that it will extend from the bifurcated part, which is bifurcated into the internal carotid artery and external carotid artery, towards the common carotid artery (step S21). For example, the size of the template 81 defines an automatic measurement area that extends about 1 cm toward the bifurcated part and toward the opposite direction, based on the location of the thickened region of the common carotid artery. In addition, the size of the template 81 is variable, and can therefore be set to a measuring physician's desired size by, for example, dragging the mouse.

Thereafter, a key is pressed by clicking a button of the mouse connected to the personal computer 5. Measurement is started. Consequently, automatic ΔiIMT measurement is executed according to the aforesaid algorithm (step S22).

Thereafter, when automatic ΔiIMT measurement is completed for all columns of pixels within the template 81, the largest value is detected and saved as PIMT in the memory (step S23).

Figure 13:
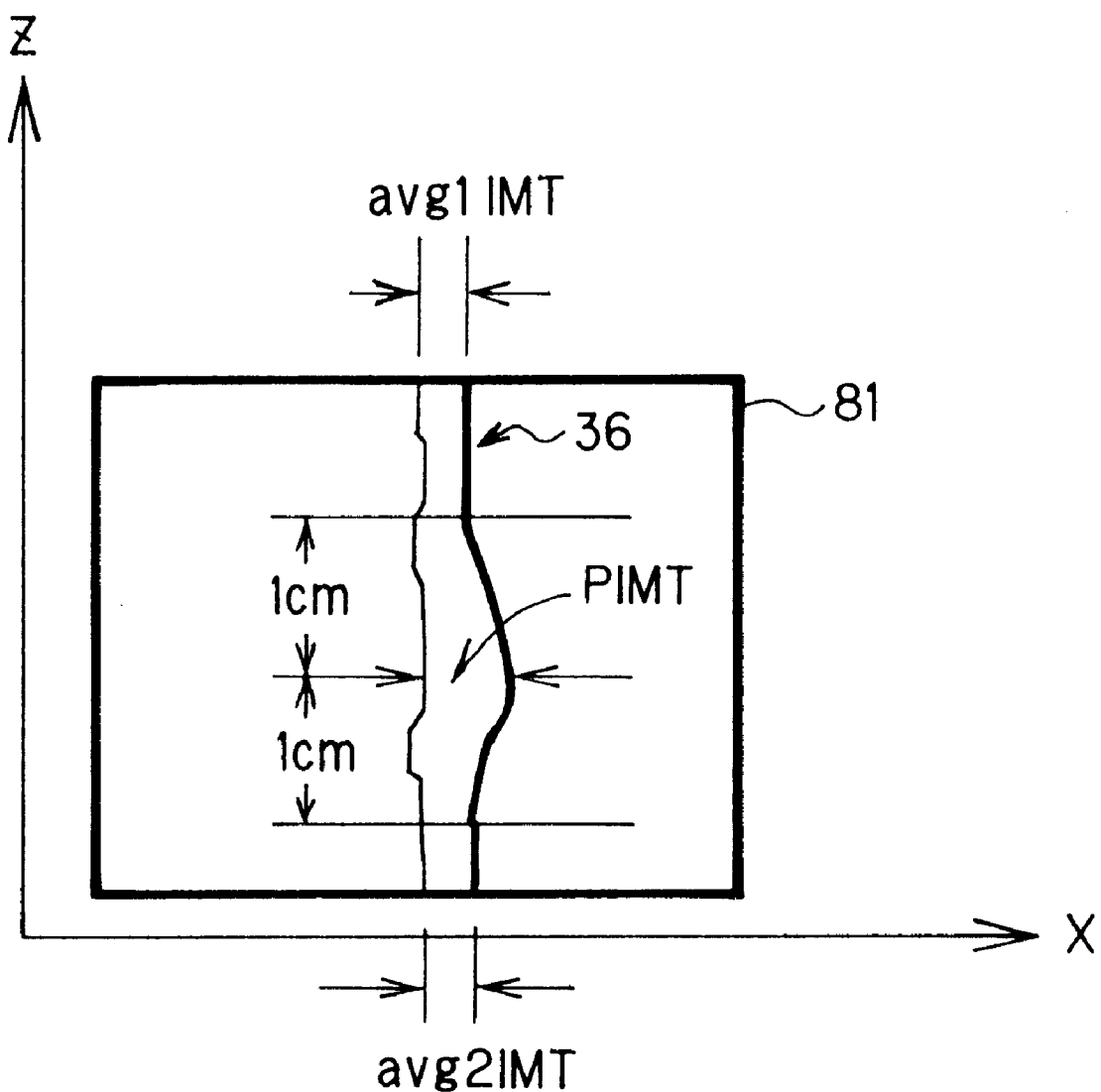
FIG. 13 is an illustration for explaining the procedure of calculating an average value at a step in the course of measurement.

Thereafter, as shown in FIG. 13, a range extending 1 cm along the Z axis with the pixel exhibiting the largest value PIMT as a center is excluded. Values of pixels on the right and left sides of the excluded range are averaged. One of the averages is regarded as avg1IMT, and the other is regarded as avg2IMT. The averages are saved in the memory (step S24). The PIMT, avg1IMT, and avg2IMT are added up and averaged. The average is output as the final value representing IMT to the screen (step S25). In the measuring system 100 of the embodiment of the present invention, the average of the IMT can be determined by using a large number of data resulting from the aforementioned measuring operation. Therefore, an accurate value representing the IMT can be obtained rapidly. In the conventional measurement using calipers, the final value representing an IMT is obtained on the basis of only a few measured values. Compared with such a manual measurement, the accuracy of the measurement of the embodiment of the present invention can be drastically increased.

Moreover, when image data to be measured contains a large amount of data like the one shown in FIG. 9E, the peak value indicating the location of the intima may not be detected many times. In this case, the aforesaid procedure is resumed from the beginning. When this problem does not occur, measurement of the carotid arteries in the five remaining lateral regions is restarted (step S26).

Thereafter, a Diagnosis key is selected by clicking a mouse button or the like. Consequently, the largest IMT value among values detected in all the six lateral regions is automatically selected and output to the screen together with an arterial sclerosis diagnosis/evaluation table (step S27). The arterial sclerosis diagnosis/evaluation table will be described. The system of this embodiment is designed not only to measure an IMT but also to diagnose and evaluate arterial sclerosis by checking measured data in comparison with actually measured intima-media values that are stored in advance. The results of the diagnosis and evaluation are output as an evaluation table. This enables proper diagnosis based on clinical data and gives a patient the motivation to take care of himself/herself.

To be more specific, IMT values actually measured from several thousands of males and females are sorted by generation and stored together with image data on a storage medium such as a hard disk in advance. Every time the aforesaid measurement is carried out, image data employed and a measured IMT value are stored. The IMT has intense correlation with aging. An average value IMTa(i) and a distribution are calculated from the stored image data for each generation. It is said that an evaluation value differs from the male and female because of menstruation and menopausal syndrome. Different evaluation tables are therefore created for the male and female.

Figure 14:
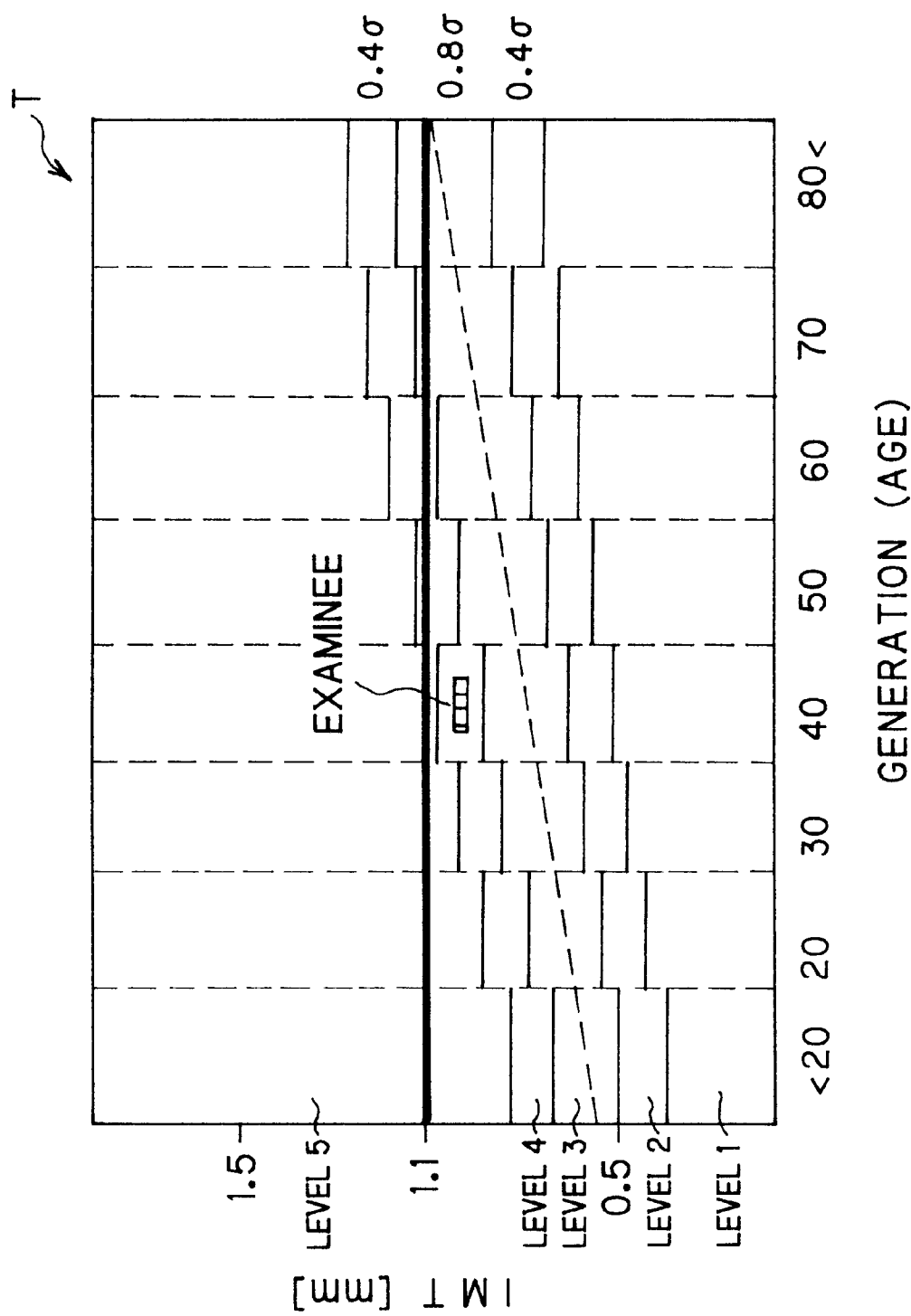
FIG. 14 shows an exemplary table for evaluating an IMT value using a variance produced by the system shown in FIG. 1.

FIG. 14 shows an example of thus created evaluation tables T. As shown in FIG. 14, evaluation levels are determined based on the distributions for each generations and sex. Three to five levels are determined. A line indicating an IMT of 1.1 mm may be drawn as a reference, and a domain of IMT values exceeding 1.1 mm may be colored in red and thus distinguished as a domain that should be noted. An examinee collates his/her own IMT value with the evaluation table to be printed out. The examinee is thus motivated to take care of himself/herself.

In the system of this embodiment, the arterial sclerosis diagnosis/evaluation table is printed out together with an IMT value to be evaluated and an ultrasonic image, and presented to the examinee (step S28).

As can be understood from the above, according to the measuring system of the embodiment of the present invention, an IMT of a carotid artery can be measured high precisely and quickly despite a simpler configuration than a conventional one. Diagnosis of arterial sclerosis can therefore be carried out more efficiently and properly. This leads to efficient and proper diagnosis of myocardial infarction, cerebral infarction, and diabetic complication. Furthermore, the history of a thrombus is stored in a database containing data of carotid arteries. This greatly contributes to quantitative diagnosis. Moreover, the present invention provides a quite inexpensive system that can be installed every clinical site. The present invention can thus contribute to smooth medical activities.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and range of equivalency of the claims therefore intended to be embraced therein.

The entire disclosure of Japanese Patent Application No. 10-135287 filed on May 18, 1998 including the specification, claims, and summary is incorporated herein by reference in its entirety.

What is claimed is:

1. An apparatus for measuring an intima-media thickness of a blood vessel, comprising:

an ultrasound device for outputting digital image data representing an image of the blood vessel produced by scanning the blood vessel with an ultrasound, the digital image data including a plurality of luminance values each corresponding to respective one of a plurality of pixels of the image; and a data analyzing device for receiving the output digital image data and calculating the intima-media thickness of the blood vessel according to the received digital image data, wherein the data analyzing device comprises:

a setting device for setting a base position between a center of the blood vessel and a position in a vicinity of an inner intima wall of the blood vessel on the image, on the basis of a moving average of the luminance values; and a calculation device for detecting a maximum value and a minimum value from among the luminance values respectively corresponding to a predetermined number of the pixels arranged from the base position toward a position of an outer adventitial wall on the image, and calculating the intima-media thickness on the basis of the maximum value and the minimum value.

2. The apparatus according to claim 1, wherein the setting device comprises a base position setting device for setting a position at which an increasing rate of the luminance values exceeds a predetermined rate as the base position.

3. The apparatus according to claim 1, wherein the thickness calculation device comprises:

a first detection device for detecting a first maximum value from among the luminance values respectively corresponding to the predetermined number of the pixels arranged from the base position toward the position of the outer adventitial wall on the image, and detecting a position of the pixel corresponding to the first maximum value as a first position;

a second detection device for detecting a second maximum value from among the luminance values respectively corresponding to the pixels arranged between the base position and the first position, and detecting a position of the pixel corresponding to the second maximum value as a second position;

a third detection device for detecting a third position at which a change of the luminance values is changed over from decrease to increase by scanning the change of the luminance values from the second position toward the center of the blood vessel, and setting the third position as a position of an inner intimal wall of the blood vessel on the image;

a fourth detection device for detecting a first minimum value from among the luminance values respectively corresponding to the pixels arranged between the first position and the second position, and detecting a position of the pixel corresponding to the first minimum value as a fourth position;

a first calculation device for calculating a position of an inner adventitial wall by using a value representing the first position and a value representing the fourth position; and a second calculation device for calculating a difference between a value representing the position of an inner intimal wall and a value representing the position of an inner adventitial wall, thereby obtaining the intima-media thickness.

4. The apparatus according to claim 3, wherein the first calculation device calculates the position of the inner adventitial wall according to an equation:

$$Xb=(MPX-MX)/2+MX,$$

where the Xb is a value representing the position of the inner adventitial wall, the MPX is a value representing the first position, the MX is a value representing the fourth position.

5. The apparatus according to claim 3, wherein the thickness calculation device comprises:

a first collecting device for collecting a plurality of values each representing the position of the inner intimal wall of the blood vessel on the image, by carrying out a detection of the position of the inner intimal wall a plurality of times at a plurality of different detecting positions, while shifting the detection position in a direction along an axis of the blood vessel;

a third calculation device for calculating a first regression curve by using the plurality of values collected by the first collection device;

a second collecting device for collecting a plurality of values each representing the position of the inner adventitial wall of the blood vessel on the image, by carrying out a detection of the position of the inner adventitial wall a plurality of times on a plurality of different detecting positions, while shifting the detection position in a direction along an axis of the blood vessel;

a fourth calculation device for calculating a second regression curve by using the plurality of values collected by the second collection device;

a fifth calculation device for calculating a plurality of thickness values respectively representing the intima-media thickness at the plurality of difference detection positions, on the basis of differences between the first regression curve and the second regression curve; and an average device for calculating an average of a maximum value among the plurality of thickness values and at least two of the plurality of thickness values except for the maximum value.

6. The apparatus according to claim 5, wherein the fifth calculation device calculates at least one of the plurality of thickness values by using a tangent of at least either one of the first regression curve and the second regression curve.

7. The apparatus according to claim 1, wherein the ultrasound device outputs a plurality of digital image data, the data analyzing device calculates the intima-media thickness of the blood vessel according to the plurality of digital image data, and the plurality of image data are obtained by scanning a part of the blood vessel with the ultrasound while changing a position from which the ultrasound is radiated.

8. The apparatus according to claim 1 further comprising:

a storage device for storing data representing intima-media thickness with respect to a plurality of examinees or patients; and an evaluation table generating device for generating an evaluation table in which data indicating averages and distributions of the intima-media thickness for each age of the examinees or patients are described.

9. The apparatus according to claim 1 further comprising an optically coupled device for optically connecting between the ultrasound device and the data analyzing device.

* * * * *